US00PP23659P2

(12) United States Plant Patent
Stemkens

(10) Patent No.: US PP23,659 P2
(45) Date of Patent: Jun. 11, 2013

(54) ***VERBENA* PLANT NAMED 'VEAZ0012'**

(50) Latin Name: *Verbena×hybrida*
Varietal Denomination: VEAZ0012

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 65 days.

(21) Appl. No.: 13/373,712

(22) Filed: Nov. 28, 2011

(51) Int. Cl.
*A01H 5/00* (2006.01)

(52) U.S. Cl.
USPC ..... Plt./308

(58) Field of Classification Search ..... Plt./308
See application file for complete search history.

*Primary Examiner* — Susan McCormick Ewoldt
(74) *Attorney, Agent, or Firm* — Joshua L. Price

(57) ABSTRACT

A new *Verbena* plant named 'VEAZ0012' particularly distinguished by the unique tri-colored flowers that are white and two distinct tones of purple-violet, lighter-medium green foliage, medium sized creeping and trailing plant habit with good branching.

1 Drawing Sheet

Latin name of the genus and species of the plant claimed: *Verbena×hybrida.*

Varietal denomination: 'VEAZ0012'.

BACKGROUND OF THE NEW PLANT

The present invention comprises a new *Verbena*, botanically known as *Verbena×hybrida*, and hereinafter referred to by the variety name 'VEAZ0012'.

'VEAZ0012' is a product of a planned breeding program. The new cultivar has unique tri-colored flowers that are white and two distinct tones of purple-violet, lighter-medium green foliage, medium sized creeping and trailing plant habit with good branching.

'VEAZ0012' originated from an open pollinated hybridization made in August 2008 in a controlled breeding environment in Enkhuizen, Netherlands. The female parent was the unpatented, proprietary plant designated 'L0510-4' with burgundy flowers, greater seed set and poor branching.

The male parent of 'VEAZ0012' was an unknown plant. The resultant seed was sown in February 2009.

'VEAZ0012' was selected as one flowering plant within the progeny of the stated cross in August 2009 in a controlled environment in Enkhuizen, Netherlands.

The first act of asexual reproduction of 'VEAZ0012' was accomplished when vegetative cuttings were propagated from the initial selection in August 2009 in a controlled environment in Enkhuizen, Netherlands.

BRIEF SUMMARY OF INVENTION

Horticultural examination of plants grown from cuttings of the plant initiated in August 2009, and continuing thereafter, has demonstrated that the combination of characteristics as herein disclosed for 'VEAZ0012' are firmly fixed and are retained through successive generations of asexual reproduction.

'VEAZ0012' has not been observed under all possible environmental conditions. The phenotype may vary significantly with variations in environment such as temperature, light intensity and day length.

A Plant Breeder's Right for this cultivar was applied for in Canada on Jun. 7, 2011, #11-7310. 'VEAZ0012' has not been made publicly available more than one year prior to the filing of this application.

The following traits have been repeatedly observed and are determined to be basic characteristics of the new variety. The combination of these characteristics distinguishes this Verbena as a new and distinct variety.

BRIEF DESCRIPTION OF THE PHOTOGRAPHS

Figure 1:
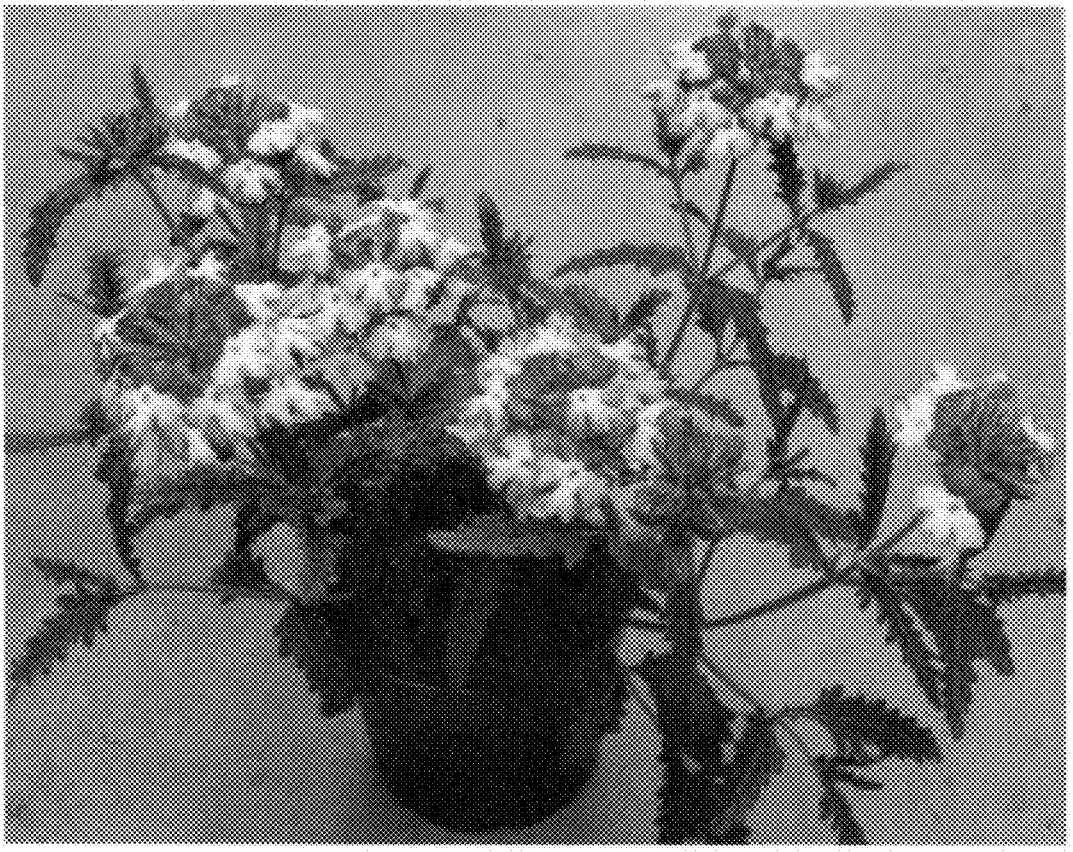
Figure 2:
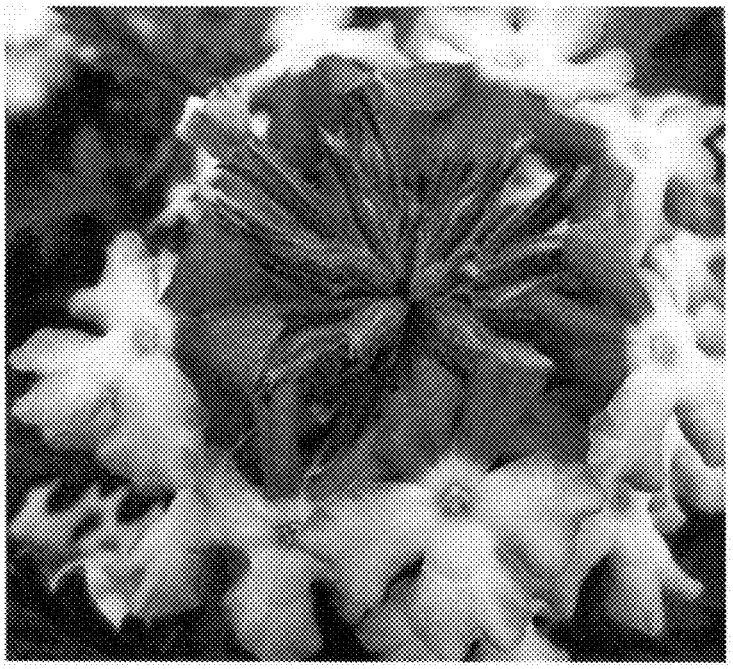

The accompanying photographic illustrations show typical flower and foliage characteristics of 'VEAZ0012' with colors being as true as possible with an illustration of this type. The photographs show in FIG. 1. a flowering plant of the new variety and in FIG. 2. a close-up of the flowers.

DETAILED BOTANICAL DESCRIPTION

The aforementioned photographs were taken in April 2011, from plants growing in a greenhouse trial in Andijk, Netherlands. These plants were grown in 10 cm pots and were approximately 13 weeks of age.

The plant descriptions and measurements were taken in May 2011 in Enkhuizen, Netherlands on about 13 week old plants that had been planted into 12 cm pots and were grown on benches in a greenhouse at a minimum temperature (heating temperature) of 12° C. From April on, a minimum night temperature of 8° C. was held, while day temperatures were much higher, depending on outdoor temperature.

Color references are made to The Royal Horticultural Society Colour Chart (R.H.S.) 2001.

TABLE 1

DIFFERENCES BETWEEN THE NEW VARIETY 'VEAZ0012' AND A SIMILAR VARIETY

| | 'VEAZ0012' | 'FLAGDENA' (U.S. Plant Pat. No. 22,438) |
|---|---|---|
| Floret size: | Smaller | Larger |
| Flower color: | Purple with white | Pink with white |
| Plant vigor: | Less vigorous | More vigorous |

Plant:

*Form, growth and habit.*—Herbaceous, initially spreading, later becoming decumbent to trailing.

*Plant height*.—About 20.0 cm.
*Plant height* (*inflorescence included*).—About 23.0 cm.
*Plant width*.—About 30.0 cm.

Roots:
*Number of days to initiate and produce roots*.—About 10-14 days at about 22 degrees C.
*Type*.—Fine, fibrous, free branching.
*Color*.—RHS N155B.

Foliage:
*Arrangement*.—Opposite, decussate on upright stems.
*Immature, leaf color, upper surface*.—RHS 143A to RHS 143B.
*Lower surface*.—RHS 141D.
*Mature, leaf color, upper surface*.—RHS 137A.
*Lower surface*.—RHS 137A to RHS 138B.
*Length*.—2.8-3.5 cm.
*Width*.—1.0-1.2 cm.
*Shape*.—Ovate.
*Base shape*.—Attenuate.
*Apex shape*.—Apiculate.
*Margin*.—Dentate, slightly pinnatifid.
*Texture, upper surface*.—Short hair, slightly glossy.
*Lower surface*.—Short stiff hair; some glandular hairs.
*Color of veins, upper surface*.—RHS 144B.
*Color of veins, lower surface*.—RHS 145B.
*Petiole color*.—RHS 145B with RHS 145C on the under side.
*Petiole length*.—0.4 cm.
*Petiole diameter*.—0.25 cm.
*Petiole texture*.—Hirtellous.

Stem:
*Characteristics*.—Side branches develop potentially at every node.
*Color of stem*.—RHS 137C.
*Length of stem*.—Approximately 8.0-20.0 cm.
*Diameter*.—0.2 cm.
*Length of internodes*.—Approximately 2.0-5.0 cm.
*Texture*.—Rough; densely covered with hair; hirsute.
*Color of peduncle*.—RHS 138B.
*Length of peduncle*.—1.5-3.0 cm.
*Peduncle diameter*.—0.2 cm.
*Texture*.—Rough, densely covered with short glandular hair; hirtellous.

Inflorescence:
*Type*.—Umbel-like, but actually a spike, umbrella-shaped to roughly semi-spherical.
*Blooming habit*.—Flowers continuously through the summer months.
*Quantity of inflorescences per plant*.—17-21.
*Lastingness of individual blooms on the plant*.—About 4 days in the greenhouse.
*Fragrance*.—Very light.
*Quantity of flowers and buds per inflorescence*.—17-35.
*Inflorescence horizontal diameter*.—5.0-6.0 cm.
*Inflorescence depth* (*height*).—2.0-3.0 cm.

Bud (just when starting to show color):
*Color*.—RHS 85D with RHS N87A margins.
*Length*.—1.8 cm.
*Width*.—0.4 cm.
*Shape*.—Mainly tube-shaped with a bulbous end.

Floret:
*Form and type*.—Sessile; salverform, composed of 5 partly fused petals with a base of a narrow tube.
*Immature color, upper surface*.—Upper two petals are RHS N81A; bottom three petals are RHS N155B but whiter with RHS N81B margins.
*Lower surface*.—RHS 84A.

Mature floret:
*Floret diameter*.—1.7-2.0 cm.
*Floret depth*.—1.8-2.0 cm.
*Floret color, upper surface*.—Upper two petals are RHS N81A; bottom three petals are RHS N155B but whiter with RHS N81B margins.
*Lower surface*.—RHS N82D.
*Length of petals*.—0.9 cm.
*Width of petals*.—0.7 cm.
*Petal shape*.—Obcordate, sometimes obovate.
*Apex shape*.—Emarginate to retuse.
*Margin*.—Entire.
*Petal texture, upper surface*.—Smooth and glabrous.
*Lower surface*.—Smooth and glabrous.
*Corolla tube length*.—1.4-2.1 cm.
*Corolla tube color inside*.—RHS 150D.
*Tube color outside*.—RHS 150D.
*Corolla texture, inside*.—Glabrous.
*Outside*.—Glabrous basally; glandular hairs at the throat opening.

Calyx:
*Type*.—Five sepals whose margins are fused to each other along their length, with a transparent membrane of less than 0.1 cm in width and with one smaller sepal attached to the base of the calyx.
*Color of sepals*.—RHS 143C.
*Length of sepals*.—1.5 cm.
*Width of sepals*.—0.2-0.3 cm.
*Sepal shape*.—Linear, fused.
*Apex shape*.—Acute.
*Margins*.—Entire.
*Texture, inner surface*.—Glabrous.
*Texture outer surface*.—Densely covered with short hair.

Reproductive organs:
*Pistil*.—1.
*Length*.—1.9 cm.
*Style color*.—RHS 150D.
*Style length*.—1.5-1.8 cm.
*Stigma color*.—RHS 138A.
*Stamens*.—Anthers and filaments fused to upper half of corolla tube; four anthers with two pollen sacs per anther.
*Color of filaments*.—RHS 150D to RHD 155B.
*Length filaments*.—0.1 cm.
*Anther color*.—RHS 144C.
*Length of anthers*.—0.1-0.15 cm.
*Color of pollen*.—RHS 1A.
*Pollen amount*.—Moderate.
*Fertility/seed set*.—Has not been observed on this hybrid.
*Disease/pest resistance*.—Has not been observed on this hybrid.

What is claimed is:

1. A new and distinct variety of *Verbena* plant named 'VEAZ0012' substantially as illustrated and described herein.

* * * * *